United States Patent
Atkinson

(10) Patent No.: US 8,555,708 B2
(45) Date of Patent: Oct. 15, 2013

(54) ROBUST SYSTEM AND METHOD FOR OBTAINING A LIQUID OR GAS SAMPLE FROM A MULTIPHASE MIXTURE FLOWING IN A HYDROCARBON PIPELINE

(75) Inventor: Ian Atkinson, Ely (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 725 days.

(21) Appl. No.: 12/513,730

(22) PCT Filed: Sep. 4, 2007

(86) PCT No.: PCT/GB2007/003304
§ 371 (c)(1),
(2), (4) Date: Sep. 24, 2009

(87) PCT Pub. No.: WO2008/056097
PCT Pub. Date: May 15, 2008

(65) Prior Publication Data
US 2010/0031754 A1    Feb. 11, 2010

(30) Foreign Application Priority Data

Nov. 9, 2006   (GB) .................................. 0622288.9

(51) Int. Cl.
*G01N 33/20* (2006.01)
*G01N 1/22* (2006.01)

(52) U.S. Cl.
USPC ..................................... 73/61.44; 73/863.21

(58) Field of Classification Search
USPC .......................................... 73/61.44, 863.21
See application file for complete search history.

(56) References Cited

U.S. PATENT DOCUMENTS

| 3,546,851 | A | * | 12/1970 | Hardison et al. ............. 96/313 |
| 4,082,004 | A | | 4/1978 | Weber et al. |
| 4,289,020 | A | | 9/1981 | Paap |
| 4,852,395 | A | * | 8/1989 | Kolpak ........................ 73/61.44 |
| 5,101,163 | A | | 3/1992 | Agar |
| 6,212,948 | B1 | | 4/2001 | Ekdahl et al. |
| 6,706,094 | B2 | * | 3/2004 | Browne ......................... 95/241 |
| 2002/0092425 | A1 | | 7/2002 | Nimberger et al. |
| 2004/0112150 | A1 | | 6/2004 | Germond |

FOREIGN PATENT DOCUMENTS

| EP | 1645863 A1 | 4/2006 |
| GB | 2319620 A | 5/1998 |
| GB | 2406386 A | 3/2005 |
| RU | 2280842 C1 | 7/2006 |

OTHER PUBLICATIONS

Combined Search and Examination Reprot of British Application No. GB 0622288.9 dated Mar. 12, 2007.
International Search Report of international application No. PCT/GB2007/003304 dated Nov. 27, 2008.

* cited by examiner

*Primary Examiner* — Hezron E Williams
*Assistant Examiner* — Nathaniel Kolb

(57) ABSTRACT

This disclosure relates in general to robust and efficient methods and systems for obtaining a sample of a liquid or gas phase from a multiphase mixture flowing in a pipeline, where the multiphase mixture comprises oil and/or a gaseous hydrocarbon and the pipeline is configured for the transport of the oil and/or gaseous hydrocarbon. In certain aspects of the present invention, after obtaining the sample of the liquid or gas phase of the multiphase mixture, sensing devices, meters, sensor systems or the like may be used to analyze the properties of the collected liquid phase sample.

30 Claims, 5 Drawing Sheets

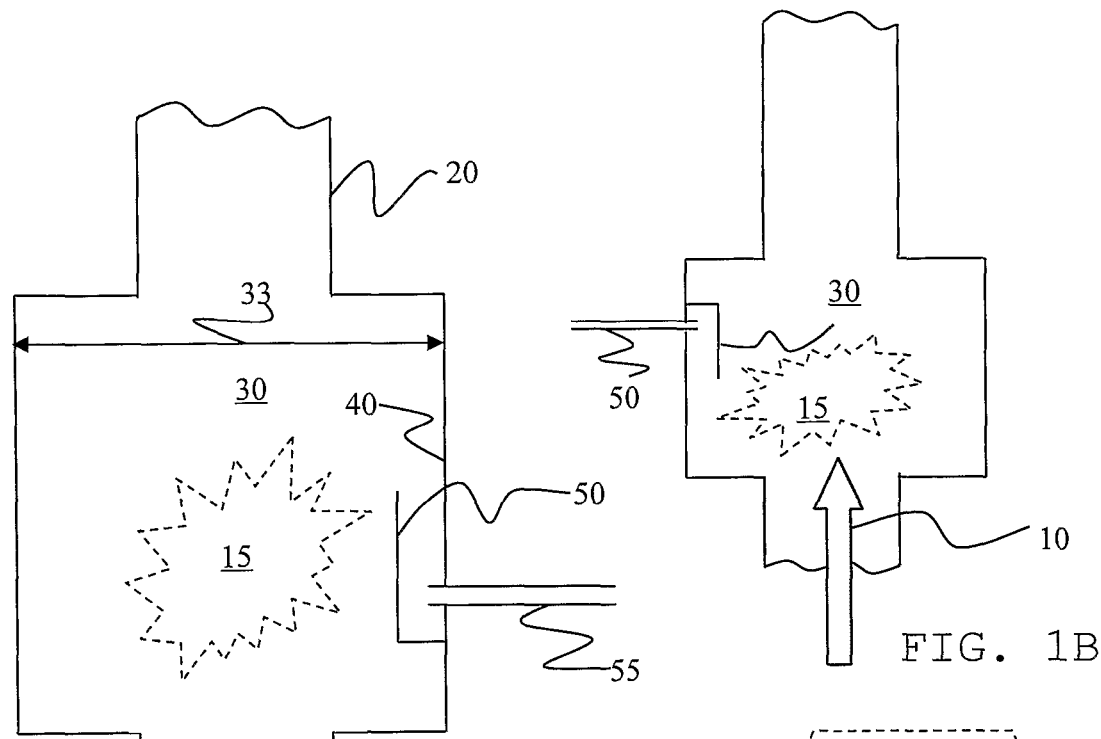
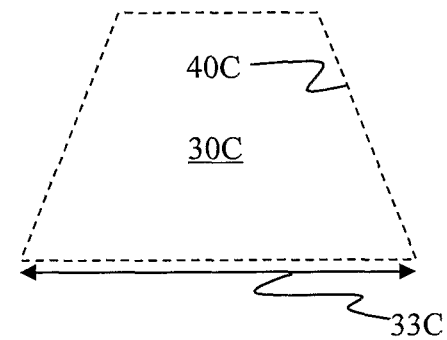
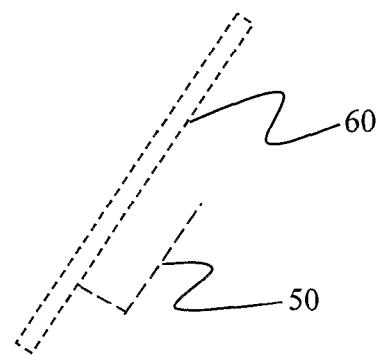
FIG. 1B
FIG. 1C
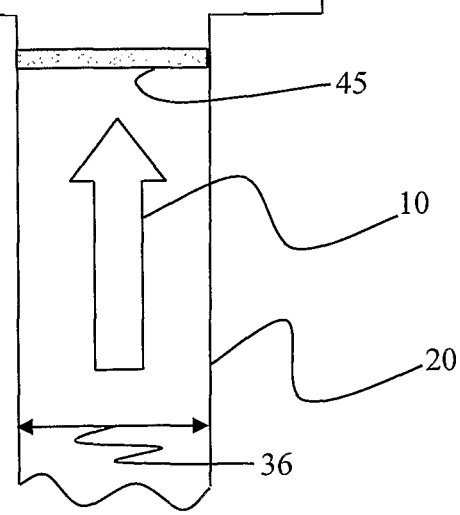
FIG. 1A
FIG. 1D

ROBUST SYSTEM AND METHOD FOR OBTAINING A LIQUID OR GAS SAMPLE FROM A MULTIPHASE MIXTURE FLOWING IN A HYDROCARBON PIPELINE

BACKGROUND OF THE INVENTION

This disclosure relates in general to robust and effective methods and systems for obtaining a sample of a liquid and/or a gas phase from a multiphase mixture flowing in a pipeline, where the multiphase mixture comprises oil and/or a gaseous hydrocarbon and the pipeline is configured for the transport of the oil and/or gaseous hydrocarbon. In certain aspects of the present invention, after obtaining the sample of the liquid or gas phase of the multiphase mixture, sensing devices, meters, sensor systems or the like may be used to analyze the properties of the collected liquid or gas phase sample.

It is desirable during the production and/or transport of oil and gas to carry out measurements to determine the properties of a multiphase mixture flowing in a hydrocarbon pipeline where the multiphase flow may consist of a combination of oil, water, gas and/or the like. With regard to the liquid phase of the multiphase mixture, measurement of the properties of the oil and/or water, including among other things the amount of the oil and/or water in a hydrocarbon transporting pipeline is often highly desirable so as to control and regulate hydrocarbon production. For example, it may be important to measure oil being produced by not only an oilfield, but also individual oil wells associated with the oilfield. Measurements may be necessary/desirable in order to determine the water and/or the gas content of the flow being produced from individual oil wells—for production analysis, etc—and/or to allocate production amounts to individual rights owners.

The early detection of water is an important measurement for subsea gas condensate wells where inhibitors may be added to prevent the formation of scale and hydrates in the pipeline downstream of the well head. In such cases, expensive inhibitors may be pumped into the pipeline from the start of hydrocarbon production, the quantity of fluid being determined from reservoir models. To manage the use of the inhibitors, the detection and quantification of the water can result in significant cost savings. Furthermore, in aging oil wells where the gas-volume fraction (GVF) can be very high (GVF >95%), the quantity of oil in the flow line determines the economics of the well.

It is, however, in general, very difficult to obtain measurements when the oil and/or water are flowing simultaneously with gaseous components through the pipeline. The problems associated with taking measurements arise, from among other things, the distribution of the different phases in the pipe—the phases may form different arrangements temporally and spatially—both axially and radially in the pipe. These different arrangements of the multiple phases may create, among other things, nonlinear responses—with the measuring system.

Flow of the multiphase fluid in the pipe may consist, among other flow designations, of a continuous phase—normally, liquid flow—or a discontinuous phase—normally, gas flow. In the continuous phase, the flow may be a continuous oil flow and the flowing oil may contain water droplets. Such flow, being primarily made up of a hydrocarbon substance, may, in general, be marked by low electrical conductance characteristics. In the alternative, the flow may be a continuous water flow with oil droplets distributed in the continuously flowing water. In such situations, the water, which may also have varying degrees of salinity, may provide that the flowing mixture has electrically conductive characteristics that change with time due to water injection or breakthrough, especially in contrast to the oil continuous situation.

With regard to the gaseous components of the multiphase fluid, the gaseous components may be distributed in large volumes or pockets in the multiphase fluid as gas churns or slugs, or may be distributed as small bubbles in the liquid phase, often referred to as bubble flow. Furthermore, under high pressure, such as found down-hole, gas in the multiphase fluid may be dissolved in the oil phase. When there are large volumes of gas in the pipeline the gas may govern the multiphase fluid flow and cause the oil and water phase to be pushed back to the pipe wall. In this case, often referred to as annular flow, the oil/water fluid mixture may move at a low velocity along the pipe wall. Additionally annular-mist flow may occur when gas flow dominates the multiphase flow in the pipe (and in mist flow, neither the water phase nor the oil phase is continuous). In such annular-mist flow, gas-carrying droplets of oil or water may move up the center of the pipe at high velocity while the remaining oil or water flows up along the pipe walls at low velocity.

In general, the liquid—which may be formed from multiple liquids mixed together—moves with a common velocity through the pipeline. However, in low flow velocity situations oil and water in the multiphase mixture may become partially or even completely separated. In such situations, the water and oil may travel at different velocities through the pipeline. For a non-horizontal pipe, the lighter oil may move up the pipe faster than the heavier water and cause small water drops to form that may in turn aggregate to form larger drops or slugs that may reach pipe diameter. This type of flow is often referred to as slug flow. The difference in velocity of the oil and water moving through the pipe is often referred to as "slip". Because gas has a substantially lower density than oil/water or a mixture of the two, a larger slip will occur between the gas and the liquid phases.

These flow properties of the multiphase mixture in the pipeline make it difficult to sample and/or measure properties of the different phases of the multiphase mixture, including the properties of the liquid phase. Sampling of the phases of the multiphase mixture are troublesome in that, generally, they require integration of equipment with the pipeline and this equipment may interfere with the efficacy and efficiency of the pipeline and, additionally, to isolate a liquid phase of the multiphase mixture may require complex equipment that may among other things, require maintenance and/or may need monitoring and controlling. As such, much of the focus of the hydrocarbon industry has focused on sensors, meter and/or the like that can directly measure properties of the multiphase mixture without sampling one or more of the phases of the multiphase mixture. Examples of some of such meters and/or sensors are described below.

U.S. Pat. No. 4,289,020 ("the '020 patent) describes a system for the limited purpose of measuring water-cut in a multiphase fluid when gas is present. The '020 patent does not disclose or teach measuring actual multiphase flow in a pipe and, consequently, it does not disclose how to address the issues associated with such measurements. The '020 patent discloses using a combined transmission-microwave and gamma-ray density measuring system to measure the water-cut in the multiphase fluid with gas present. In the system, the microwave and gamma ray beams are configured obliquely with respect to the flow axis of the multiphase fluid through the pipe that is being measured. Water-cut is calculated directly from the amplitude attenuation of the microwaves passing through the multiphase fluid and the transmission of gamma rays through the multiphase fluid.

The method disclosed in the '020 patent has many limitations including but not limited to: the method is not robust—there is no solid physical basis for determining oil/water fraction purely from microwave attenuation; determining water cut based on amplitude attenuation may be inaccurate due to nonlinear attenuation effect; and the method does not provide for the use of low activity radiation sources. U.S. Pat. No. 5,101,163 ("the '163 patent) discloses measuring water fraction in an oil/water mixture by using at least one transmitting antenna and two receiving antennas. As disclosed, antennas are designed to emit and receive operating frequencies around 2.45 GHz through the multiphase fluid. The phase difference and/or the power ratio of the two received signals are determined and used with a look-up table to yield water fraction. The '163 patent discloses installing the antennas axially in such a way that one receiving antenna receives signal in the flow direction, while the other equally-spaced antenna receives its signal against the flow direction to provide for measurement of the phase difference of signals received by the two antennas, which is directly related to the flow velocity. The '163 patent does not disclose how to make corrections for instabilities in the flow due to gas nor does it disclosed how the microwave receivers' amplitude/phase difference or ratio measurements at 2.45 GHz compensate for changes in water salinity—different water salinities will cause the multiphase fluid containing the water to interact differently with the microwaves and to cause different amplitude attenuations and phase shifts.

Many of the techniques for evaluating hydrocarbon containing multiphase mixtures flowing in a pipeline have involved attempting to accurately measure the water or the oil fraction in the multiphase flow. Techniques to make such measurements, as discussed above, have included measuring electrical impedance, microwave transmission, optical attenuation, acoustic attenuation, acoustic scattering or the like across the multiphase mixture flowing in the pipeline. However, the difficulty of making such measurement and/or analyzing the properties of the multiphase mixture from such measurements is illustrated by the fact that in a 99% GVF flow with 10% water-liquid ratio, the water occupies only 0.1% of the cross-sectional area and the oil only occupies 0.9% of the cross sectional area. Therefore, to accurately measure the liquid phase of the multiphase flow using such techniques is very difficult given that the accuracy of the fraction measurement is ~1%.

The examples above illustrate the limitations that may exist in direct measurement of phase properties of multiphase mixtures without sampling. In the hydrocarbon industry, analysis of the multiphase mixture may be necessary-desired in extreme and/or remote locations, such as down wellbores—where temperature and pressure may be very high—in subsea pipelines, in subsurface locations that may also be under the sea or the like. In such remote and/or extreme locations, it may be desirable for the analysis system to be robust, maintenance free and to provide for only limited interference with the transport of hydrocarbons in the pipelines. As such there exists a long felt need in the art for robust, versatile and effective method and system for sampling the liquid phase of a multiphase mixture flowing in a hydrocarbon transporting pipeline.

SUMMARY OF THE INVENTION

Embodiments of the present invention provide systems and methods for withdrawing samples of a liquid or gas phase from a multiphase mixture containing one or more hydrocarbons flowing in a pipeline. More specifically, but not by way of limitation, embodiments of the present invention address the long felt need in that art, described above, by providing robust and effective systems and methods for obtaining samples of the liquid or gas phase of the multiphase mixture containing the one or more hydrocarbons flowing in the pipeline using expansion and/or radially outward flow of the gas phase of the multiphase mixture as a part of a phase separation method or system.

In one embodiment of the present invention, an expansion conduit is coupled with a hydrocarbon transporting pipeline, the expansion conduit has an inner volume with a cross-sectional size that is greater than that of the pipeline or a restrictor pipe positioned upstream of the expansion conduit to allow for expansion and/or radially outward flow of the gas phase of the multiphase mixture in the expansion conduit. In such an embodiment, a liquid phase sampler may be disposed within the inner volume and coupled with a depositing surface to collect a sample of the fluid phase of the multiphase mixture deposited on the depositing surface and collected in the sampler when the multiphase mixture is dispersed by the expansion and/or radially outward flow of the gas phase in the expansion conduit. In certain aspects, the fluid phase deposited on the depositing surface and collected in the sampler is withdrawn from the expansion conduit for analysis. The rate of withdrawal of the fluid phase may be controlled by, among other things, physical properties of the depositing surface, collector and/or the withdrawal apparatus, such that any gas contained in the fluid phase may escape from the liquid phase prior to the fluid phase exiting the expansion conduit through the withdrawal apparatus.

In a further embodiment, a gas phase collection system may comprise an expansion conduit coupled with a hydrocarbon transporting pipeline, the expansion conduit may have an inner volume with a cross-sectional size that is greater than that of the pipeline or a restrictor pipe positioned upstream of the expansion conduit to allow for expansion and/or radially outward flow of the gas phase of the multiphase mixture in the expansion conduit. In certain aspects, an annulus formed between an inside surface of the expansion conduit and an outside surface of a pipe section transporting the multiphase mixture into the expansion conduit or an independent gas collector may be positioned in the expansion chamber to provide that a portion of the gases expanding and/or flowing outward in the expansion chamber collect in the annulus or the gas collector. A sampling outlet may be used to remove a sample of the gas phase collected in the gas collector and a sensor coupled with the sampling outlet may be used to analyze the sample of the gas phase flowing in the sampling outlet.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

The invention will be better understood in the light of the following description of non-limiting and illustrative embodiments, given with reference to the accompanying drawings, in which:

FIG. 1A provides a schematic-type illustration of a system for sampling a liquid phase of a multiphase mixture containing hydrocarbons flowing through a conduit, in accordance with an embodiment of the present invention;

FIG. 1B provides a schematic-type illustration of a system for sampling a gas phase of a multiphase mixture containing hydrocarbons flowing through a conduit, in accordance with an embodiment of the present invention FIG. 1C illustrates an expansion chamber for a system for sampling a liquid phase of a multiphase mixture containing hydrocarbons flowing through a conduit, in accordance with an embodiment of the present invention;

FIG. 1D illustrates an independent depositing surface that may be used in a system for collecting a liquid phase of a multiphase hydrocarbon mixture flowing in a pipeline, in accordance with an embodiment of the present invention.

DETAILED DESCRIPTION OF THE INVENTION

Figure 2A:
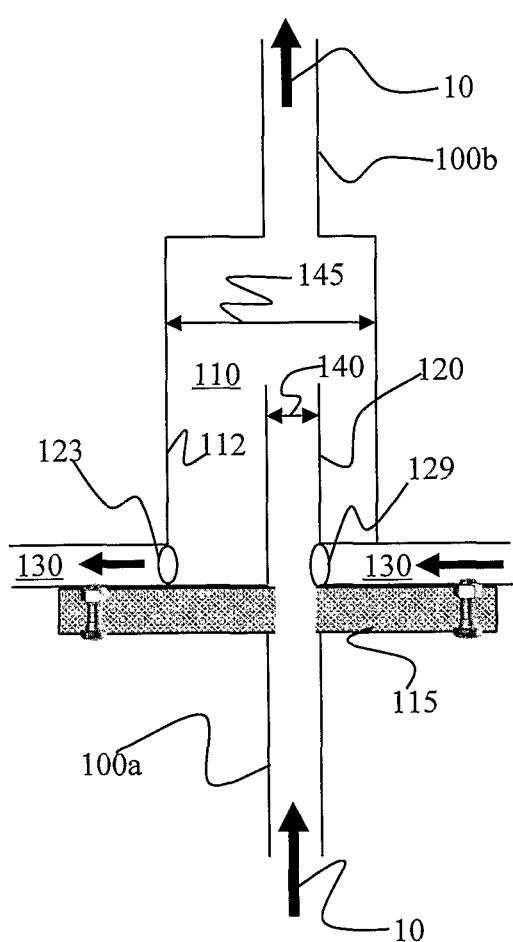
FIG. 2A is a schematic-type illustration of a system for sampling a liquid phase of a multiphase mixture containing hydrocarbons flowing through a conduit, in accordance with an embodiment of the present invention.

Embodiments of the present invention provide systems and methods for obtaining samples of liquid phases of multiphase mixtures containing one or more hydrocarbons flowing in a conduit. More specifically, but not by way of limitation, certain embodiments of the present invention provide robust systems and methods with minimal moving parts or the like that allow for separating liquids in a multiphase mixture containing a hydrocarbon, such as oil, methane or the like, from the multiphase mixture. After sampling, the liquid phase sample may be analyzed/measured to determine one or more physical properties of the sampled liquid phase—which may comprise oil, water and/or the like. Analysis of the liquid phase separately from the multiphase mixture may have many advantages, including accuracy, not requiring complex/multi-component sensors and/or meters and/or the like.

FIGS. 1A-C provides schematic-type illustrations of systems for sampling a liquid phase of a multiphase mixture containing hydrocarbons flowing through a conduit, in accordance with embodiments of the present invention.

In FIG. 1A, a multiphase mixture 10 is flowing through a pipeline 20. The flow through the pipeline may be either upward or downward through the pipeline. The multiphase mixture 10 contains one or more hydrocarbons. These hydrocarbons may be liquid hydrocarbons, such as oil or the like and/or gaseous hydrocarbons, such as methane, propane, butane and/or the like. The multiphase mixture may contain other components such as water, hydrogen sulphide, carbon dioxide and/or the like. The pipeline 20 may be a pipeline configured for transporting hydrocarbons, a pipe/conduit associated an oilwell/wellbore, a subsea transportation pipeline and/or the like.

In FIG. 1A an expansion chamber 30 is integrated with the pipeline 20. In certain aspects of the present invention, the expansion chamber 30 may not be directly integrated with the pipeline 20, but may be integrated with a deviating pipe system that is connected to the pipeline 20 and through which a portion of the multiphase mixture 10 may be deviated from the main flow in the pipeline 20. In other embodiments of the present invention, a restrictor (not shown) may be positioned in the pipeline 20 to reduce the internal size of the pipeline 20 and the expansion chamber 30 may be a section of the pipeline 20 located downstream of the restrictor into which the multiphase mixture flows after flowing through the restrictor.

The expansion chamber 30 may have an internal size 33, where the internal size 33 defines a maximum size of an internal cross-section of the expansion chamber 30. Where the expansion chamber 30 is a cylinder or the like, the internal size 33 is the internal diameter of the cylinder. However, in alternative aspects of the present invention, the expansion chamber 30 may have a shape other than cylindrical and, in such aspects, the internal size 33 will be a maximum size of a cross-section of the non-cylindrical shape.

The pipeline 20 may have an internal diameter 36 characterizing an internal diameter of the pipeline 20. In an embodiment of the present invention, the internal size 33 is larger than the internal diameter 36. In aspects where the expansion chamber 30 is connected to a deviation pipe or the like connected to the pipeline 20, the internal size 33 may be larger than an internal diameter of the deviation pipe or the like. In other embodiments of the present invention where the expansion chamber 30 is a section of the pipeline 20 located downstream of the restrictor into which the multiphase mixture flows after flowing through the restrictor, the pipeline may have an internal diameter that is greater than an internal diameter of the restrictor.

Because the expansion chamber 30 has a larger cross-section than the immediately preceding conduit, the expansion chamber 30 may allow for an expansion and/or radially outward flow of the gas phase 15 of the multiphase mixture 10. The expansion and/or radially outward flow of the gas phase 15 in the expansion chamber may cause the liquid phase of the multiphase mixture 10 to be dispersed. The multiphase mixture may have a gas rich core that upon entering the expansion chamber 30 may cause liquid in the multiphase mixture to be sprayed outwards. The dispersal pattern of the liquid phase of the multiphase mixture 10 in the expansion chamber 30 may be affected by, among other things, the flow of the multiphase mixture, the physical properties of the expansion chamber 30 and/or the like. Merely by way of example, in an embodiment where both the pipeline 20 and the expansion chamber 30 are cylindrical, the liquid phase may be dispersed radially outward but with a forward trajectory that may result from the flow of the multiphase mixture 10 in the pipeline 20.

In an embodiment of the present invention, the liquid phase of the multiphase mixture 10 dispersed in the expansion chamber 30 may be deposited on a surface in the expansion chamber 30.

As depicted in FIG. 1A, an inner surface 40 of the expansion chamber 30 may comprise a depositing surface on which the liquid sprayed outwards from the multiphase mixture 10 in the expansion chamber 30 may be deposited. In other aspects of the present invention, the depositing surface may be wholly or partially independent from the expansion chamber 30, the inner surface 40 and/or the like. In such aspects, computer modeling, experimentation and/or the like may be used to determine where and how to position the deposition surface relative to the pipeline 20, expansion chamber 30, flow of the multiphase mixture 10 and/or the like to achieve the desired depositing of the liquid phase of the multiphase mixture 10.

As described above, the multiphase mixture 10 may flow through the pipeline 20 in a wide variety of flow configurations, i.e. the majority of the liquid phase flowing on the inner surface of the pipeline 20, the liquid phase flowing as droplets in the gaseous phase etc. These flow configuration may affect the depositing of the liquid phase on the inner surface 40 and may cause, among other things, unrepresentative depositing of certain constituents of the liquid phase on the inner surface 40, i.e. more water than oil may be deposited on the inner surface 40 because of the flow characteristics of the water and the oil prior to entry into the expansion chamber 30. As such, as compared to the composition of the multiphase mixture 10, certain liquids may be over represented in the liquid phase deposited on the inner surface 40. In certain aspects of the present invention, a flow mixer 45 may be incorporated downstream of the expansion chamber 30 to provide for mixing of the multiphase mixture. This mixing prior to the depositing of at least a portion of the liquid phase of the multiphase mixture 10 on the inner surface 40 may provide that the deposited liquids are representative of the composition of the liquid phase of the multiphase mixture 10.

The flow mixer 45 may comprise a nozzle, a flow constrictor, a series of vanes designed to swirl the flow of the multiphase mixture 10 and/or the like.

In an embodiment of the present invention, a sample collector 50 may be coupled with the inner surface 40. The sample collector 50 may be configured with the inner surface 40 to provide that at least a portion of the liquids deposited on the inner surface 40 is collected in the sample collector 50. A sampling conduit 55 may be coupled with the sample collector 50 to provide for flow out of the expansion chamber 30 of a sample of the liquid phase of the multiphase mixture 10 collected in the sample collector 50.

The liquid phase of the multiphase mixture 10 deposited on the inner surface 40 may be entrained with some of the gaseous phase of the multiphase mixture 10. In certain aspects of the present invention, the inner surface 40, the sample collector 50 and/or the sampling conduit 55 may be configured so that that flow of the liquid phase out of the sample collector 50 is configured to provide that the entrained gas escapes from the liquid phase prior to the liquid phase exiting the expansion chamber 30 through the sampling conduit 55. In certain aspects, physical dimensions of the sample inner surface 40, the sample collector 50 and/or the sampling conduit 55 may be used to control a flow rate of the collected liquid phase to provide for the escape of gas. In other aspects, components such as baffles, valves and/or the like may be used to control flow of the liquid phase to provide for gas escape from the collected liquid phase.

In certain embodiments of the present invention, a sensor, meter and/or the like (not shown) may be coupled with the sampling conduit 55 and may provide for sensing/measuring properties of the sample of the liquid phase flowing in the sampling conduit. In certain aspects, because only the liquid phase of the multiphase mixture 10 is flowing in the sampling conduit 55, a basic "off-the-shelf" sensor, meter and/or the like may be used to determine an amount of oil, water or other liquid in the sampling conduit 55 from which a corresponding amount in the multiphase mixture 10 flowing in the pipeline 20 may be extrapolated. As such, the systems and methods of the present invention may provide efficient/effective means for determining, among other things, water fraction (cut) and/or oil fraction (cut), where:

Oil Fraction=1−Water Fraction

In an embodiment of the present invention, a liquid hydrostatic head created by the liquid phase collected in the sample collector 50 may cause the flow of the liquid phase in the sampling conduit 55. By analyzing the frictional resistance to this flow, the flow rate can be determined for a particular liquid phase sampling system, in accordance with an embodiment of the present invention. The flow rate for the liquid phase sampling system may be determined by modeling, experimentation and/or the like. In certain aspects of the present invention, the flow rate of the liquid phase may be configured to provide for the prevention of the blocking of flow or other detrimental effect of solids in the multiphase mixture 10. A pump or the like (not shown) may also be coupled with the sampling conduit 55 to provide for controlling flow through the sampling conduit 55 and/or for moving particulate build up by increasing the flow of the liquid phase or back-flushing.

In some embodiments of the present invention, the sampling conduit 55 may be configured to flow the sample of the liquid phase of the multiphase mixture 10 out of the pipeline 20 for analysis by one or more sensors/meters and back through an aperture into the pipeline 20. In such aspects, none of the multiphase mixture 10 may be permanently removed from the pipeline 20. To prevent collection of particulate/solids in the sampling conduit 55, in some embodiments of the present invention, the sampling conduit may be configured to be horizontal. In other, embodiments the sampling conduit 55 may exit the pipeline 20 at one vertical position and provide for flow of the sampled liquid phase back into the pipeline 20 at a lower vertical position so as to provide for "washing" particulates/solids out of the sample collector 50 and/or the sampling conduit 55. In such configurations, flow restrictors, valves or the like may provide for controlling the flow of the liquid phase. In yet other aspects of the present invention, other flow paths for the sample of the liquid phase collected in the sample collector 50 may be provided by the sampling conduit 55 and/or other conduits associated with the sampling conduit 55 or the sample collector 50.

In the embodiment of the present invention depicted in FIG. 1A, the pipeline 20 is configured to provide for vertical flow of the multiphase mixture 10 and the multiphase mixture 10 is depicted flowing vertically upwards through the pipeline 20 and the expansion chamber 30. In other embodiments of the present invention, multiphase mixture 10 may flow vertically downwards through the pipeline 20 and the expansion chamber 30. In yet other embodiments, the pipeline and/or the expansion chamber 30 may be at other orientations with the inner surface 40, the sample collector 50 and/or the sampling conduit 55 at appropriate orientations relative to the expansion chamber 30 and/or the pipeline to provide for collection of a sample of the dispersed liquid phase in the sample collector 50 and flowing of the sample of the collected liquid phase through the sampling conduit 55.

FIG. 1B illustrates a further embodiment of the present invention in which the system of FIG. 1A may, essentially, be inverted, to provide for collection of a sample of a gas phase of a multiphase mixture. In such a configuration as depicted in FIG. 1B, the sample collector 50 may be facing downwards with the opening at the top of the sample collector 50 facing towards the multiphase mixture 10 flowing into the expansion chamber 30. In such an embodiment, a gas phase of the multiphase mixture 10 may expand and/or flow outward from a centre of the expansion chamber 30 when the multiphase mixture enters the expansion chamber 30. This outwardly flowing gas phase may flow along an inner wall of the expansion chamber 30 and may be trapped and/or collected by the sample collector 50. In certain aspects, channels, grooves, barriers, valves and/or the like may be disposed in the expansion chamber 30 to provide for channeling the gas phase to the sample collector 50. The channels, grooves, barriers, valves and/or the like may provide for separating the gas phase from the liquid phase, increasing collection of the gas phase and/or the like.

As discussed above, a portion of the outflowing/expanding gas phase may be collected in the sample collector 50. The sampling conduit 55 may then be used to draw of a sample of the gas phase collected in the sample collector 50. In such embodiments, due to the sample collector 50 being configured such that liquids and/or heavier phases of the multiphase mixture 10 may flow out of the sample collector 50 under gravity, the sample collector 50 may be used to provide for collection of the lighter phases and/or gas phase of the multiphase mixture 10. In certain aspects, a pump, a valve and/or the like coupled with the sampling conduit 55 may be used to provide for the drawing off of a sample of the gas phase of the multiphase mixture 10 from the sample collector 50. A sensor, meter and/or the like may be coupled with the sampling conduit 55 to provide for analysis of the gas phase flowing in the sampling conduit 55.

In a further embodiment of the present invention, two collectors may be used, one configured to collect a sample of a liquid phase of the multiphase mixture and one configured to collect a sample of a gas phase of the multiphase mixture. In certain aspects, the two collectors may be configured so that the liquid phase collector and the gas phase collector are essentially mirror images of each other.

In certain aspects, due to differences in densities of components of the gas phase, the sampling conduit 50 may be coupled with the sample collector 50 to provide for preferential sampling of certain gas components. In other aspects the sampling conduit 50 may be variably coupled with the sample collector 50 to control which gas components are being sampled.

FIG. 1C illustrates an expansion chamber 30C for a liquid phase sampling system in accordance with an embodiment of the present invention. The expansion chamber 30C may have an internal size 33C characterizing a maximum internal diameter or the like of the expansion chamber 30C. The internal size 33C may be configured to be larger than an internal diameter of a pipeline (not shown) that the expansion chamber 30C is to be coupled with. As such, the gas phase of the multiphase mixture flowing in the pipeline may expand/flow partially outward in the expansion chamber 30C causing dispersion of the liquid phase of the multiphase mixture.

As depicted, the expansion chamber 30C has a sloping internal surface 40C that may provide for depositing of the liquid phase of the multiphase mixture. Flow of the liquid phase deposited on the inner surface 40C may provide for collection in a collector (not shown) coupled with the inner surface 40C.

FIG. 1D illustrates an independent depositing surface 60 that may be used in a system for collecting a liquid phase of a multiphase-hydrocarbon mixture flowing in a pipeline, in accordance with an embodiment of the present invention. The independent depositing surface 60 may be disposed within and/or coupled with an expansion chamber to provide for depositing on the independent depositing surface 60 a sample of the liquid phase of the multiphase mixture containing one or more hydrocarbons flowing from a pipeline into the expansion chamber. A sample collector 50 may be coupled with the independent depositing surface 60 to provide for collection of at least a portion of the sample of the liquid phase deposited onto the independent depositing surface 60. A sampling conduit (not shown) may provide for flowing the collected sample of the liquid phase to one or more sensors/meters for analysis. The sampling conduit may flow the liquid phase collected in the sample collector 50 out of the pipeline and/or expansion chamber for analysis or the one or more sensor/meters may be positioned in the pipeline and/or expansion chamber and coupled with the sampling conduit to provide that none of the systems components is external to the pipeline and/or expansion chamber.

The independent depositing surface 60 may be positioned at different locations in and/or orientations to the expansion chamber. In some aspects, the independent depositing surface 60 may be moveable and management of the depositing/collection of the liquid phase by the independent depositing surface 60 may be controlled.

FIG. 2A provide a schematic-type illustration of a system for sampling a liquid phase of a multiphase mixture containing hydrocarbons flowing through a conduit, in accordance with an embodiments of the present invention. In the depicted system, the multiphase mixture 10 is flowing in a transportation conduit 100a configured for transporting hydrocarbons. The transportation conduit 100a may be hydrocarbon transportation pipe, a pipe associated with transporting hydrocarbons in or from a hydrocarbon producing wellbore or the like.

In some aspects, the transportation conduit 100a may be directly coupled with an expansion conduit 110. In other aspects, the transportation conduit 100a may be coupled with an entrance conduit 120 that is in turn coupled with the expansion conduit 110. In either aspect, in certain embodiments of the present invention, the transportation conduit 100a or the entrance conduit 120 may be coupled with the expansion conduit 110 by a coupler 115 and may be configured so that a portion of the transportation conduit 100a or the entrance conduit 120 extends into an interior volume of the expansion conduit 110, where the interior volume is defined by an inner surface 112 of the expansion conduit 110.

Figure 2B:
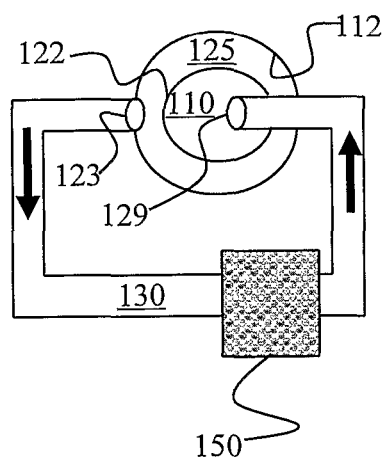
FIGS. 2B and 2C depict bird's-eye-type views of horizontal slices through systems for sampling a liquid phase of a multiphase mixture containing hydrocarbons flowing through a conduit, in accordance with embodiments of the present invention.
Figure 2C:
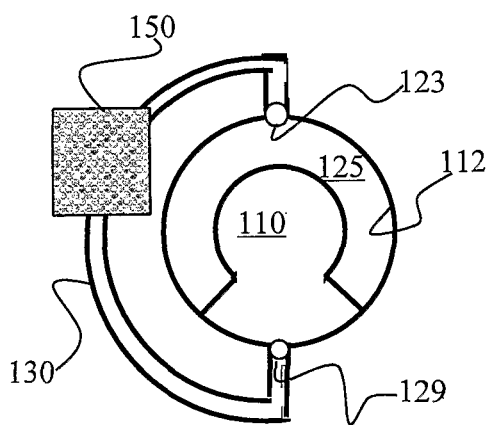

FIGS. 2B and 2C depict bird's-eye-type views of horizontal slices through systems for sampling a liquid phase of a multiphase mixture containing hydrocarbons flowing through a conduit, in accordance with embodiments of the present invention.

FIG. 2B illustrates how, by extending the transportation conduit 100a or the entrance conduit 120 into the interior volume of the expansion conduit 110, an annulus 125 may be formed in the space between an outer surface 122 of the transportation conduit 100a or the entrance conduit 120 and the inner surface 112 of the expansion conduit 110. In accordance with some embodiments of the present invention, the expansion conduit 110 may have an inner diameter 145 and the transportation conduit 100a or the entrance conduit 120 may have an inner diameter 140. In an embodiment of the present invention, the inner diameter 145 may be larger than the inner diameter 140 to provide that the gas phase of the multiphase mixture 10 flowing into the expansion conduit 110 may expand and/or flow outwards from a gas rich core of the multiphase mixture 10.

As a result of the outward-type flow of the gas phase of the multiphase mixture 10, a portion of the liquid phase of the multiphase mixture 10 may be dispersed in the expansion conduit 110 and deposited on the inner surface 112. In the embodiment of the present invention depicted in FIGS. 2A and 2B, the portion of the liquid phase of the multiphase deposited on the inner surface 112 may be transported under gravity into the annulus 125. In FIG. 2B, the annulus 125 may comprise essentially the full circumference of the outer surface 122 of the transportation conduit 100a or the entrance conduit 120. In certain aspects, however, the outer surface 122 of the transportation conduit 100a or the entrance conduit 120 may be configured in various ways to vary the size of the annulus 125, as shown in FIG. 2C.

A sampling inlet 123 in the inner surface 112 may provide for fluid communication between a sample flowline 130 and the annulus 125 to allow for flow of the sample of the liquid phase collected in the annulus 125 into the sample flowline 130. By varying the physical dimension of the sampling inlet 123 and the sample flowline 130 the rate of flow of the sample of the liquid phase may be controlled to provide that any gas in the liquid phase may escape before the sample of the liquid phase enters the sample flowline 130.

The sample flowline 130 may be coupled with a sensor 150 to provide for measurement/analysis of one or more properties of the sample of the liquid phase of the multiphase mixture 10 flowing in the sample flowline 130. Merely by way of example, the sensor 150 may measure a percentage of water and/or oil in the sample of the sample of the liquid phase and from this information a percentage of oil and or water flowing in the multiphase mixture 10 may be extrapolated. Furthermore, in other examples, an amount of water and oil in the liquid sample may be calculated and using flow data of the multiphase mixture 10 in the transportation conduit 100a, the flow rate of the liquid sample in the sample flowline 130 and/or the like flow rates and/or amounts of liquid elements in the transportation conduit 100a may be extrapolated.

In certain embodiments of the present invention, the sample flowline 130 may be in fluid communication with the expansion conduit 110 via a sampling outlet 129. In this way, the sample of the liquid phase may be returned to the expansion conduit 110 and/or transportation conduit 100a and may be returned to flow with the gas phase of the multiphase mixture 10 out of the liquid phase sampling system via exit conduit 100b.

The sampling outlet 129 may be positioned to provide that the sample flowline 130 is horizontal. As such, the sample of the liquid phase flowing out of the sampling outlet 129 may be re-sampled. Analysis of such re-sampling may only minimally influence the sampling process. However, screening-type techniques or the like may be used to prevent re-sampling of the sampled liquid phase exiting the sampling outlet 129. In some aspects, the sampling outlet 129 may be lower than the sampling inlet 123 to provide that the sample flowline 130 is vertically tilted to use gravity to provide a force to act on the sample of the liquid phase in the sample flowline 130. Use of gravitational forces in such a way may help provide for moving solid-type debris or viscous fluids through the expansion conduit 110. In other aspects, the sampling outlet 129 may be higher than the sampling inlet 123. In such aspects, the sample of the liquid phase flowing out of the sampling outlet 129 may not be re-sampled. Furthermore, in such aspects, a pump, hydrostatic head pressure and/or the like may provide for the flow of the sample of the liquid phase through the sample flowline 130

FIG. 2C illustrates a bird's-eye-type view of a horizontal slice through a system comprising a partial annulus-liquid-phase-sample-collector for sampling a liquid phase of a multiphase mixture containing hydrocarbons flowing through a conduit, in accordance with embodiments of the present invention. In such an embodiment, only a partial annulus/ partial circumferential collector 125 may be used to collect the liquid phase of the multiphase mixture 10 dispersed onto the inner surface 112.

Figure 3:
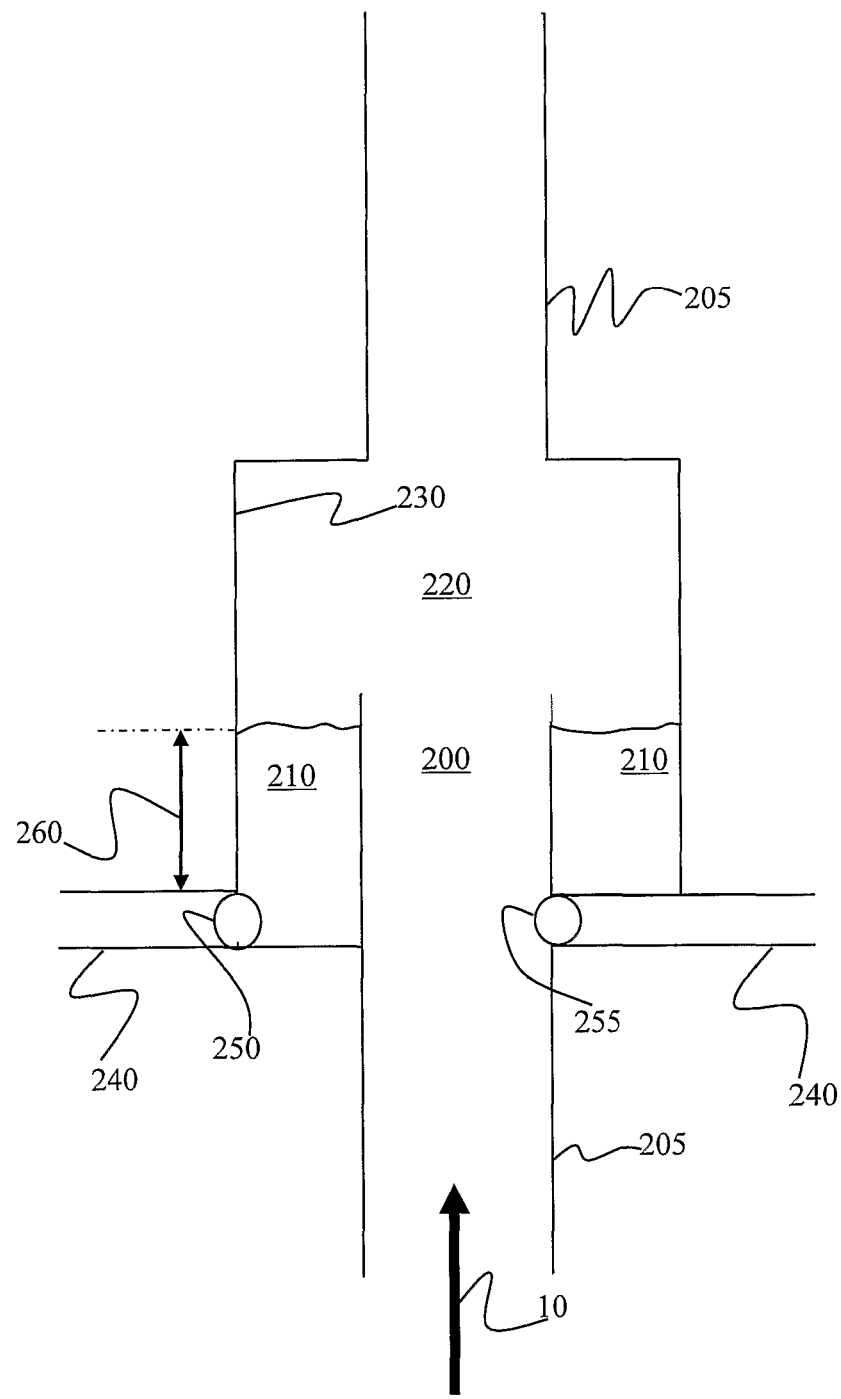
FIG. 3 is a schematic-type illustration of a system for sampling a liquid phase of a multiphase mixture containing hydrocarbons flowing through a conduit with various sampling parameters depicted, in accordance with an embodiment of the present invention.

FIG. 3 is a schematic-type illustration of a system for sampling a liquid phase of a multiphase mixture containing hydrocarbons flowing through a conduit with various sampling parameters depicted, in accordance with an embodiment of the present invention. As depicted, the multiphase mixture 10 may flow vertically upward through a main flow pipeline 205 and pass into a channel 200 formed by an annulus 210 that may occupy all or part of a circumference of an expansion section 220; the annulus 210 may be closed at the bottom and open at the top. On exiting the main flow pipeline 205, the multiphase mixture 10 may have a gas rich core that may expand, essentially, outwards and may cause liquid in the multiphase mixture 10 to be sprayed outwards from a centre line of the expansion section 220 towards an inner walls 230 of the expansion section 220. Some of this dispersed liquid may hit the inner walls 230 and drain into the annulus 210.

In the annulus 210, gas in the liquid may be separated by buoyancy—since gas-liquid separation is significantly faster than liquid-liquid separation. By controlling the flow rate of the collected liquids out of the annulus 210, such buoyancy separation of the gas and liquid may provide for complete or almost complete separation of any gas from the liquid in the annulus 210.

A liquid return pipe 240 may be in fluid communication with the annulus 210 and may provide a connection between a bottom of the annulus 210 and the main flow pipeline 205. Water fraction and/or the like may be measured in the liquid return line 240 by a water-in-oil sensor or the like. Merely by way of example, a water-in-oil sensor based on capacitance measurements may be used since the dielectric constant of water is ~80 and the dielectric constant of hydrocarbon is ~2. In other aspects, sensors based upon microwave transmission and/or reflection, resonant frequencies, conductivity and/or the like may be used in the sensing device.

In some embodiments of the present invention, the annulus 210 may occupy only part of the circumference of the main flow pipeline 205 to provide for a configuration in which the return line 240 allows for sampled liquid to be returned at the circumference of the main flow pipeline 205, which may minimize the likelihood of sampling the same fluid twice. As noted above, and depicted in FIG. 3, in some embodiments, the annulus 210 may occupy the entire circumference of the main flow pipeline 205.

It may be assumed that the sample of liquid collected in the liquid sampling system described is representative of that in the main flow pipeline 205 because of the mixing that occurs at the exit of the main flow pipeline 205 into the expansion section 220.

However, even if the collected liquid sample is not representative of the liquid components of the multiphase mixture 10, the system may allow for the detection of water, oil and/or the like, but not the quantification. As noted previously, a mixer may be used in conjunction with the present sampling components of the present invention to provide for mixing of the multiphase mixture 10 prior to sampling of the liquid phase.

The liquid flow through the liquid return line 240 between an inflow point 250 and an outflow point 255 may result from a liquid hydrostatic head in the annulus 220 that is created because of the frictional pressure drop in the line joining the inflow point 250 and the outflow point 255. Accordingly, if v is the liquid velocity in the return line 240, the liquid return line 240 having a diameter D and a length L, then:

$$v^2 \propto \frac{Dgh}{fL}$$

where f is the friction factor, g is the acceleration due to gravity and h is the height of the liquid 260 in the annulus 210. In the present system, there may always be a height of liquid in the annulus 210 when liquid is being collected and, as a consequence, by positioning the inflow point 250 and the outflow point 255 appropriately, the liquid return line 240 may be maintained full of a sample of the liquid phase.

Sand, particulates or the like in the main flow in the main flow pipeline 205 may be sampled in the annulus 210 where it will initially accumulate because of the low velocities in this region. Some sand may pass into the liquid return line 240 where, in certain aspects, accumulation may be minimized by ensuring that the velocity in the liquid return line 240 is high enough to carry the particles and/or vertical upwards flow in the liquid return line 240 is minimized or avoided. A flow of greater than about 0.8 m/s in the liquid return line 240 may prevent accumulation of particulates or the like in the liquid return line 240. In certain aspects, a grate or mesh, a settling tank type structure, a swirling flow system and/or the like may be coupled with the liquid return line 240 to provide for collection/removal of solids/particulates from the sample of the liquid phase.

Figure 4:
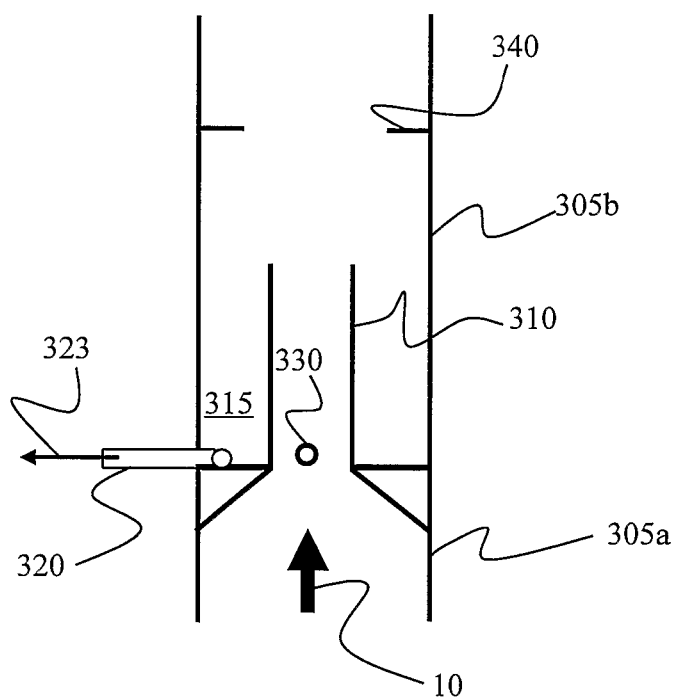
FIG. 4 illustrates a system for sampling a liquid phase of a multiphase mixture containing hydrocarbons flowing through a conduit incorporating a flow restrictor conduit and an orifice plate, in accordance with an embodiment of the present invention.

FIG. 4 illustrates a system for sampling a liquid phase of a multiphase mixture containing hydrocarbons flowing through a conduit incorporating a flow restrictor conduit and an orifice plate, in accordance with an embodiment of the present invention. In an embodiment of the present invention, the multiphase mixture 10 flowing in a pipeline 305a may be constricted by a constriction conduit 310. The constriction conduit 310 may have a smaller internal size than the pipeline 305a.

An expansion conduit 305b, which may in some aspects be a section of the pipeline 305a may have a cross-section, internal diameter or the like (depending upon the shape of the expansion conduit 305b) that is larger than the internal cross-section of the constriction conduit 310 and may allow for an expansion and/or radially outward flow of the gas phase of the multiphase mixture, which may have previously been in a gas rich core of the multiphase mixture 10.

The liquid phase of the multiphase mixture may be deposited on an interior surface of the constriction expansion conduit 305b as a result of the expansion/or radially outward flow of the gas phase of the gas phase. Gravitational forces may provide for collection of the deposited liquid phase in a sample collector 315 coupled with the interior surface. A sample line 320 may provide for a flow depicted by arrow 323 of a sample of the liquid phase of the multiphase mixture 10 in the sample line 320. An opening 330 in one end of the sample line 320 may provide for flow of the sample of the liquid phase back into the expansion conduit 305b.

In certain aspects, the quantity of the liquid phase collected in the sample collector 315 may be increased by use of an orifice plate 340 that may be positioned downstream of the sample collector 315. In such aspects, a gas core of the multiphase mixture exiting the channel formed by the constriction conduit 310 may pass through the centre of the orifice plate 340, whereas the liquid(s) of the multiphase mixture 10 may be deflected upon exiting constriction conduit 310 onto the walls of the expansion conduit 305b and/or orifice plate 340 from where the liquid(s) may drains into the sample collector 315. The illustrated device may also work for a vertically downward flow with the collector facing upstream.

Figure 5:
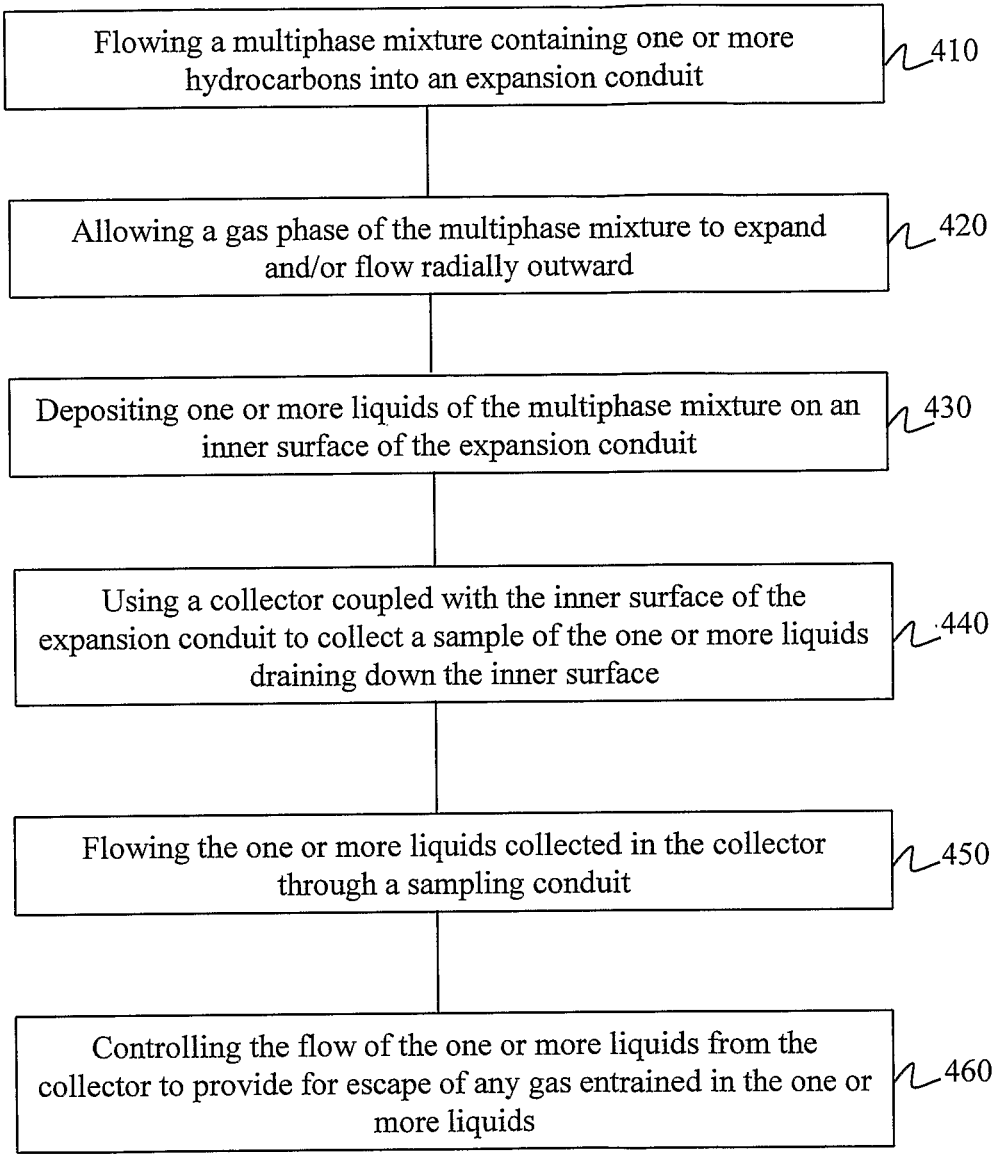
FIG. 5 is a flow-type representation of a process for sampling a liquid phase of multiphase mixture flowing in a pipeline, conduit or wellbore configured for carrying hydrocarbons, in accordance with an embodiment of the present invention.

FIG. 5 is a flow-type representation of a process for sampling a liquid phase of multiphase mixture flowing in a pipeline, conduit or wellbore configured for carrying hydrocarbons, in accordance with an embodiment of the present invention. In accordance with an embodiment of the present invention, in step 410 a multiphase mixture containing one or more hydrocarbons that is in a conduit—which may be a wellbore pipe, a transportation pipeline or the like—may be flowed into an expansion conduit. The expansion conduit may be a conduit with an internal cross-section that is larger than the cross-section of the preceding pipe or conduit through which the multiphase mixture was flowing. Where the multiphase mixture is flowing in a pipeline, the expansion chamber may be a section of pipe with a larger internal diameter than the pipeline or it may be section of the pipeline located proximal to a restriction in the pipeline through which the multiphase mixture flows.

In step 420, a gas phase of the multiphase mixture may expand and/or flow essentially radially outward upon entering the expansion conduit. In step 430, the expansion and/or radially outward flow of the gas phase may cause deposition of liquids in the multiphase mixture on an inner surface of the expansion chamber.

In step 440, a collector coupled with the inner surface of the expansion conduit may be used to collect a sample of the one or more liquids draining down the inner surface. In step 440, the collector may be positioned so that gravity causes at least a portion of the deposited liquids to drain into the collector.

In step 450, the one or more liquids collected in the collector may be flowed through a sampling conduit. The sampling conduit may flow the one or more liquids our of the expansion chamber or, in some embodiments, to a sensor in the expansion chamber. In embodiments where the sampling conduit flows the one or more liquids out of the expansion chamber, one or more sensors may be disposed outside the expansion chamber and coupled with the sampling conduit to provide for sensing of the liquids.

In step 460 the flow of the one or more liquids from the collector through the sampling conduit may be controlled to provide for escape of any gas entrained in the one or more liquids before the one or more liquids enters the sampling conduit. Gas escape may be due to buoyancy of the gas and/or the like. Control of the flow rate may be provided by valves, dimensions of the components of the system, and/or the like. In certain aspects, the one or more liquids may be flowed from the sampling conduit back into the expansion chamber and/or the pipeline.

In the foregoing description, for the purposes of illustration, various methods and/or procedures were described in a particular order. It should be appreciated that in alternate embodiments, the methods and/or procedures may be performed in an order different than that described.

Hence, while detailed descriptions of one or more embodiments of the invention have been given above, various alternatives, modifications, and equivalents will be apparent to those skilled in the art without varying from the spirit of the invention. Moreover, except where clearly inappropriate or otherwise expressly noted, it should be assumed that the features, devices and/or components of different embodiments can be substituted and/or combined. Thus, the above description should not be taken as limiting the scope of the invention, which is defined by the appended claims.

What is claimed is:

1. A system for sampling a liquid phase of a multiphase mixture containing one or more hydrocarbons flowing in a pipeline configured for transporting the one or more hydrocarbons, comprising:

an expansion conduit configured for coupling with the pipeline for transporting the one or more hydrocarbons, the expansion conduit comprising a first end, a second end, an inner surface, an inner volume defined by the inner surface and the first and the second end, a first opening in the first end and a second opening in the second end, wherein:
  the first end of the expansion conduit is configured to couple with a first section of the pipeline to provide for flow of the multiphase mixture out of the pipeline through the first opening in the expansion conduit into the inner volume of the expansion conduit;
  the second opening is configured to couple with a second section of the pipeline to provide an outlet for the multiphase mixture to flow out of the inner volume into the pipeline;
  a first cross-sectional size of a section of the first section of the pipeline is smaller than a second cross-sectional size of the inner volume; and
  the expansion conduit is configured in use to be integrated with a vertical section of the pipeline and provide for unobstructed vertical flow of the multiphase mixture through the expansion conduit;
a fluid phase collector coupled with the inner surface and configured to provide that a portion of the fluid phase of the multiphase mixture deposited on the inner surface when the multiphase mixture flows through the expansion conduit travels down the inner surface under gravity and is collected in the fluid phase collector; and
a sampling conduit in fluid communication with the fluid phase collector and configured to flow the portion of the fluid phase collected in the fluid phase collector out of the fluid phase collector through the sampling conduit, wherein the flow of the portion of the fluid phase through the sampling conduit is produced in use by a hydrostatic head of the fluid phase collected in the fluid phase collector.

2. The system of claim 1, wherein the fluid phase collector and the sampling conduit are configured to provide that a flow rate of the portion of the fluid phase through the sampling conduit provides for escape of gas from the portion of the fluid phase prior to the portion of the fluid phase flowing out of the fluid phase collector through the sampling conduit.

3. The system of claim 1, wherein the sampling conduit is in fluid communication with the expansion conduit and configured to provide that the portion of the fluid phase flowing out of the fluid phase collector flows through the sampling conduit and into the expansion conduit.

4. The system of claim 3, wherein the sampling conduit is horizontal.

5. The system of claim 3, wherein the fluid phase collector and the sampling conduit are configured to provide that a flow rate of the portion of the fluid phase through the sampling conduit is sufficient to remove particulates from the sampling conduit.

6. The system of claim 5, wherein the flow rate is greater than 0.8 m/s.

7. The system of claim 1, further comprising a sensor coupled with the sampling conduit and configured to analyze the portion of the fluid phase flowing through the sampling conduit.

8. The system of claim 7, wherein the sensor is a water-in-oil sensor.

9. The system of claim 1, further comprising a flow mixer coupled with the first section of the pipeline and configured to mix the multiphase mixture.

10. The system of claim 1, further comprising an orifice plate coupled with the inner surface at a location downstream from the fluid phase collector and configured to provide for increased depositing of the fluid phase in the expansion conduit.

11. A system for sampling a liquid phase of a multiphase mixture flowing in a pipeline configured for transporting one or more hydrocarbons, comprising:
  an expansion assembly configured to couple with the pipeline for transporting one or more hydrocarbons, said expansion assembly comprising an entrance conduit and an expansion conduit, wherein:
    the expansion conduit comprises a cylinder with a first cylinder end, a second cylinder end and an inner cylinder surface;
    the inner cylinder surface has an internal diameter and defines an interior volume of the expansion conduit between the first cylinder end and the second cylinder end;
    the entrance conduit comprises a pipe with a first pipe end and a second pipe end and an external pipe surface, the external pipe surface configured to have a diameter that is smaller than the internal diameter of the expansion conduit;
    the first pipe end of the entrance conduit is coupled with a first section of the pipeline to provide for flow of the multiphase mixture from the pipeline into the entrance conduit;
    a portion of the entrance conduit including the second pipe end is disposed within the interior volume of the expansion conduit configured so that the inner cylinder surface and the external pipe surface define an annulus, wherein the annulus has a closed based and is configured to provide that at least a portion of any liquids deposited on the inner surface by expansion of the multiphase mixture in the expansion conduit will flow down the inner surface under gravity and collect in the annulus, and wherein the entrance conduit provides for flow of the multiphase mixture through the entrance conduit into the inner volume; and
    the expansion assembly is configured in use to be coupled with a vertical section of the pipeline and provide for a vertical flow of the multiphase mixture through the sampling system;
  a sampling conduit in fluid communication with the annulus and configured to provide for flow of the liquids collected in the annulus from the annulus into the sampling conduit, wherein the annulus and the sampling conduit are configured such that in use a hydrostatic head of the liquid collected in the annulus produces a flow of the collected liquid through the sampling conduit; and
  a sensor coupled with the sampling conduit and configured to sense properties of the liquid flowing in the sampling conduit, wherein the system for sampling the liquid phase of the multiphase mixture is configured to provide for.

12. The system of claim 11, wherein the sampling conduit is in fluid communication with the entrance conduit and configured to provide that the liquids collected in the annulus flow from the annulus through the sampling conduit and into the entrance conduit.

13. The system of claim 12, wherein the sampling conduit is horizontal.

14. The system of claim 11, wherein the sensor is an oil-in-water sensor.

15. The system of claim 11, further comprising a flow mixer coupled with the first section of the pipeline and configured to mix the multiphase mixture.

16. The system of claim 11, further comprising an orifice place coupled with the expansion conduit at a location downstream from the annulus and configured to provide for increased depositing of the fluid phase in the expansion conduit.

17. A method for sampling a liquid phase of a multiphase mixture containing one or more hydrocarbons flowing in a pipeline configured for transporting the one or more hydrocarbons, comprising:
   flowing the multiphase mixture from a first section of the pipeline through a second section of the pipeline, wherein the first and the section sections are inline and the flow of the multiphase mixture from the first section through the second section is unobstructed;
   causing the multiphase mixture to have an outward flow in the second section of the pipeline, wherein the outward flow comprises a flow outward from a central axis of the second section towards an inner surface of the second section of the pipeline;
   depositing the liquid phase of the multiphase mixture in the outwardly flowing multiphase mixture on a depositing surface;
   positioning a collector so that in use a portion of the liquid phase of the multiphase mixture deposited on the depositing surface flows under gravity down the depositing surface into the collector;
   using a hydrostatic head of the portion of the liquid phase of the multiphase mixture in the collector to produce a flow in a sampling conduit; and
   sensing properties of the portion of the liquid phase of the multiphase mixture flowing in the sampling conduit.

18. The method according to claim 17, wherein the step of causing the multiphase mixture to have an outward flow in the second section of the pipeline is provided by configuring the first and the second section of the pipeline such that the first section has a first internal diameter, the second section has a second internal diameter and the first internal diameter is less than the second internal diameter.

19. The method of claim 17, wherein the depositing surface is the inner surface of the second section of the pipeline.

20. The method of claim 17, wherein the depositing surface is a surface disposed within the second section of the pipeline.

21. The method of claim 20, wherein the depositing surface is adjusted to different orientations in the second section of the pipeline.

22. The method of claim 21, wherein the depositing surface may be adjusted during sampling of the liquid phase.

23. The method of claim 17, wherein the first section comprises a constriction in the pipeline.

24. The method of claim 23, further comprising the step of using a mixer to mix the multiphase mixture before flowing the multiphase mixture into the second section of the pipeline.

25. The method of claim 17, wherein the step of sensing properties of the portion of the liquid phase of the multiphase mixture flowing in the sampling conduit comprises sensing an oil to water ratio of the liquid phase.

26. The method of claim 17, further comprising the step of using an orifice plate to increase an amount of the liquid phase of the multiphase mixture deposited on the depositing surface.

27. The method of claim 17, further comprising the step of flowing the portion of the liquid phase of the multiphase mixture flowing in the sampling conduit into the second section of the pipeline.

28. The method of claim 17, further comprising the step of controlling a flow rate of the liquid phase of the multiphase mixture flowing in the sampling conduit to provide for escape of gas from the liquid phase prior to the liquid phase entering and flowing through the sampling conduit.

29. The method of claim 17, wherein the liquid phase of the multiphase mixture is flowed horizontally through the sampling conduit.

30. The method of claim 17, wherein a flow rate of the liquid phase of the multiphase mixture through the sampling conduit is high enough to prevent build-up of particulates in the sampling conduit.

* * * * *